(12) United States Patent
Hadani

(10) Patent No.: US 8,360,968 B2
(45) Date of Patent: Jan. 29, 2013

(54) ENDOSCOPIC SHEATH WITH ILLUMINATION

(75) Inventor: Ron Hadani, Cresskill, NJ (US)

(73) Assignee: Vision—Sciences Inc., Orangeburg, NY (US)

( * ) Notice: Subject to any disclaimer, the term of this patent is extended or adjusted under 35 U.S.C. 154(b) by 1175 days.

(21) Appl. No.: 11/792,146

(22) PCT Filed: Dec. 1, 2005

(86) PCT No.: PCT/US2005/043272
§ 371 (c)(1),
(2), (4) Date: Aug. 12, 2008

(87) PCT Pub. No.: WO2006/060457
PCT Pub. Date: Jun. 8, 2006

(65) Prior Publication Data
US 2009/0036739 A1    Feb. 5, 2009

Related U.S. Application Data

(60) Provisional application No. 60/632,739, filed on Dec. 1, 2004, provisional application No. 60/653,135, filed on Feb. 16, 2005, provisional application No. 60/669,007, filed on Apr. 7, 2005.

(51) Int. Cl.
*A61B 1/06* (2006.01)

(52) U.S. Cl. .................. 600/178; 600/121; 600/182

(58) Field of Classification Search .................. 396/14, 396/17; 600/120–124, 172, 178, 182
See application file for complete search history.

(56) References Cited

U.S. PATENT DOCUMENTS

| | | | |
|---|---|---|---|
| 3,610,231 A * | 10/1971 | Takahashi et al. | 600/139 |
| 4,475,555 A | 10/1984 | Linder | |
| 4,594,074 A | 6/1986 | Andersen et al. | |
| 4,763,659 A | 8/1988 | Dunseath, Jr. | |
| 4,890,623 A | 1/1990 | Cook et al. | |
| 4,960,133 A | 10/1990 | Hewson | |
| 5,069,215 A | 12/1991 | Jadvar et al. | |
| 5,179,952 A | 1/1993 | Buinevicius et al. | |
| 5,289,555 A * | 2/1994 | Sanso | 385/92 |
| 5,343,860 A | 9/1994 | Metzger et al. | |
| 5,386,817 A * | 2/1995 | Jones | 600/104 |
| 5,704,892 A | 1/1998 | Adair | |
| 5,782,896 A * | 7/1998 | Chen et al. | 607/88 |
| 6,449,006 B1 * | 9/2002 | Shipp | 348/70 |
| 6,468,204 B2 * | 10/2002 | Sendai et al. | 600/160 |
| 6,478,730 B1 | 11/2002 | Bala et al. | |
| 6,567,990 B1 | 5/2003 | Spitznagle | |

(Continued)

FOREIGN PATENT DOCUMENTS

| | | |
|---|---|---|
| DE | 3327561 | 3/1984 |
| DE | 4238977 | 5/1994 |

(Continued)

OTHER PUBLICATIONS

International Preliminary Report on Patentability Dated Jun. 14, 2007 From the International Bureau of WIPO Re.: Application No. PCT/US2005/043272.

(Continued)

*Primary Examiner* — Clayton E Labelle
*Assistant Examiner* — Warren K Fenwick

(57) ABSTRACT

A protective sheath adapted to cover an elongate medical probe. The sheath includes an elongate sheath adapted to receive an insertion tube of a medical probe and isolate the insertion tube from body tissue and at least one light generating element mounted on the sheath.

24 Claims, 4 Drawing Sheets

U.S. PATENT DOCUMENTS

| | | | |
|---|---|---|---|
| 6,584,347 B1 | 6/2003 | Sinderby | |
| 6,616,655 B1 | 9/2003 | Falwell et al. | |
| 6,623,423 B2* | 9/2003 | Sakurai et al. | 600/104 |
| 6,764,581 B1 | 7/2004 | Forrow et al. | |
| 7,276,066 B2* | 10/2007 | Ouchi | 606/46 |
| 2002/0193842 A1 | 12/2002 | Forsell | |
| 2003/0229267 A1 | 12/2003 | Belson et al. | |
| 2004/0162584 A1 | 8/2004 | Hill et al. | |
| 2004/0230096 A1 | 11/2004 | Stefanchik et al. | |
| 2005/0197534 A1 | 9/2005 | Barbato et al. | |
| 2005/0234298 A1* | 10/2005 | Kucklick et al. | 600/156 |
| 2005/0283065 A1* | 12/2005 | Babayoff | 600/407 |
| 2006/0116564 A1 | 6/2006 | Mintchev et al. | |
| 2007/0213590 A1* | 9/2007 | Squicciarini | 600/172 |
| 2007/0270653 A1* | 11/2007 | Vayser et al. | 600/182 |
| 2008/0249507 A1 | 10/2008 | Hadani | |

FOREIGN PATENT DOCUMENTS

| | | |
|---|---|---|
| DE | 19703737 | 8/1998 |
| EP | 1449488 | 8/2004 |
| EP | 1459695 | 9/2004 |
| EP | 1502543 | 2/2005 |
| WO | WO 00/74556 | 12/2000 |
| WO | WO 2006/060457 | 6/2006 |
| WO | WO 2006/060458 | 6/2006 |
| WO | WO 2006/060459 | 6/2006 |

OTHER PUBLICATIONS

International Preliminary Report on Patentability Dated Jun. 14, 2007 From the International Bureau of WIPO Re.: Application No. PCT/US2005/043273.

International Preliminary Report on Patentability Dated Jun. 14, 2007 From the International Bureau of WIPO Re.: Application No. PCT/US2005/043274.

Official Action Dated Mar. 24, 2011 From the US Patent and Trademark Office Re. U.S. Appl. No. 11/791,985.

International Search Report and the Written Opinion Dated Apr. 19, 2006 From the International Searching Authority Re.: Application No. PCT/US2005/043273.

International Search Report and the Written Opinion Dated Aug. 30, 2006 From the International Searching Authority Re.: Application No. PCT/US2005/043272.

Official Action Dated May 12, 2010 From the US Patent and Trademark Office Re.: U.S. Appl. No. 11/792,147.

Written Opinion Dated May 3, 2006 from the International Searching Authority Re.: Application No. PCT/US2005/043274.

International Search Report Dated May 3, 2006 from the International Searching Authority Re.: Application No. PCT/US2005/043274.

* cited by examiner

ENDOSCOPIC SHEATH WITH ILLUMINATION

RELATED APPLICATIONS

This Application is a National Phase of PCT Patent Application No. PCT/US2005/043272 having International Filing Date of Dec. 1, 2005, which claims the benefit under 119(e) of U.S. provisional patent application 60/632,739, titled "Add on Electrode for Endoscope", filed Dec. 1, 2004, U.S. provisional patent application 60/653,135, titled "Endoscopic Sheath with Illumination System", filed Feb. 16, 2005, and U.S. provisional patent application 60/669,007, filed Apr. 7, 2005, titled "Emergency Electrode on Medical Tube". The disclosures of all of these applications are incorporated herein by reference.

FIELD OF THE INVENTION

The present invention relates to sheaths for medical apparatus.

BACKGROUND OF THE INVENTION

Endoscopes are used to view internal tissue of humans, and for many other tasks. As sterilization of endoscopes is relatively difficult, disposable sheaths which cover an endoscope are often used to isolate the endoscope from the patient tissue, so as to avoid time-consuming cleaning and disinfection processes.

In many cases, in order to view the interiors of body cavities, there is a need for delivery of illumination to body cavities.

U.S. Pat. No. 6,449,006 to Shipp, the disclosure of which is incorporated herein by reference, describes an illumination system including a plurality of light emitting diodes (LEDs) for an endoscopic camera. The system includes twenty eight LEDs mounted on a ceramic substrate having a cylindrical aperture, which allows light from a viewed object to reach a lens of the endoscope.

U.S. Pat. No. 6,814,699 to Ross et al., the disclosure of which is incorporated herein by reference, describes an endoscope including an array of LEDs mounted on a substrate and covered by a common distal protective shield. The array may be mounted at the distal end of an insertion tube of the endoscope.

U.S. Pat. No. 6,551,240 to Henzler, the disclosure of which is incorporated herein by reference, describes an endoscope with illumination LEDs.

U.S. patent publication 2004/0064018 to Dunki-Jacobs et al., the disclosure of which is incorporated herein by reference, describes an endoscope that has an integrated light source and camera mounted at the distal end of the endoscope.

The above patent publications all describe endoscopes which are specifically planned with LEDs mounted thereon. Using the description of any of these patents requires replacing currently used endoscopes at a relatively high cost.

PCT publication WO2004/000107 to Couvillon, the disclosure of which is incorporated herein by reference, describes an endoscope with a sensor disposed at a distal end of the endoscope and a portable power source which can be disposed anywhere along the length of the endoscope but is preferably located at a proximal end of the endoscope.

U.S. Pat. No. 6,478,730 to Bala, the disclosure of which is incorporated herein by reference, describes a laparoscope having a disposable sheath which leads illumination within its walls to a distal end of the laparoscope. The leading of illumination through the walls of a thin protective sheath has encountered various technical problems.

U.S. Pat. No. 5,165,387 to Woodson, the disclosure of which is incorporated herein by reference, describes a disposable endoscope kit, which has a disposable light source for mounting at a proximal end of a channel of the endoscope kit, within the channel.

SUMMARY OF THE INVENTION

An aspect of some embodiments of the present invention relates to a protective sheath of an endoscope, which includes one or more light sources, such as illumination LEDs, mounted on or within the protective sheath. A potential advantage of mounting LEDs on the protective sheath, is providing illumination with an endoscope that does not include a built in illumination system or to provide additional illumination when the illumination provided by the built in illumination of the endoscope is insufficient. The LEDs are optionally mounted on a distal end of the sheath. In some embodiments, the sheath does not interfere with the lighting, as may occur if the LEDs are on the endoscope.

The LEDs optionally do not include a protective lens, which would add to the size of the protective sheath. Alternatively, the LEDs have a minimal size protective layer which protects the LED and/or protects the sheath from the heat of the LED.

An aspect of some embodiments of the present invention relates to a protective sheath of an endoscope, which includes a power source, such as a battery, embedded in the sheath (or mounted on the sheath), for powering light sources, control circuits, ablation electrodes and/or any other elements requiring power. In some embodiments of the invention, the power-requiring elements are mounted on the sheath or are otherwise coupled to the sheath. Using a battery mounted on or in the sheath, can eliminate the need to run wires (or at least power carrying wires) along the sheath and/or to connect the sheath to a power source external to the sheath.

In some embodiments of the invention, instead of or in addition to embedding a battery in the sheath, a receiver (or antenna) for wirelessly receiving power is embedded in the sheath. Further alternatively or additionally, a piezo-electric power source, for example which converts pressure on the sheath and/or movements of the sheath into electrical power, is mounted on the sheath.

In other embodiments of the invention, wires along the sheath are used to connect the battery (e.g., for recharging) and/or LEDs, or other power using elements (e.g., a camera), to an external power source. The wires may be embedded within the sheath or may run along the inside or outside of the wall of the sheath.

An aspect of some embodiments of the invention relates to mounting a camera on a sheath. The sheath above the camera is optionally formed as a lens, which leads light to the camera. In some embodiments of the invention, the camera is attached to the sheath on an inner surface of the sheath. Alternatively, the camera is mounted within the sheath or on an outer surface of the sheath.

There is therefore provided in accordance with an exemplary embodiment of the invention, a protective sheath adapted to cover an elongate medical probe, comprising an elongate sheath adapted to receive an insertion tube of a medical probe and isolate the insertion tube from body tissue and at least one light generating element mounted on the sheath.

Optionally, the at least one light generating element comprises at least one light emitting diode. Optionally, the at least one light generating element comprises at least one chemiluminescent vial. Optionally, the at least one light generating element is mounted within three centimeters of a distal end of the sheath. Optionally, the at least one light generating element is mounted on a distal face of the sheath. Optionally, the sheath includes a battery electrically coupled to the light generating element, at least partially embedded within the sheath. Optionally, the sheath includes at least one optic element adapted to change a direction of light emitted by one or more of the at least one light generating element.

There is further provided in accordance with an exemplary embodiment of the invention, a protective sheath for an endoscope, comprising an elongate sheath adapted to receive an insertion tube of an endoscope and isolate the insertion tube from body tissue and a power source, such as a battery at least partially embedded within the sheath.

Optionally, the battery is at least partially embedded within the sheath within five centimeters from a distal end of the sheath. Optionally, the sheath includes a wireless power reception port, coupled to the sheath, adapted to wirelessly receive power from a power transmitter external to the sheath. Optionally, the battery is rechargeable. Optionally, the battery has a length at least ten times longer than its width. Optionally, the battery comprises a plurality of links connected through wires. Optionally, the battery does not substantially affect the flexibility of the sheath. Optionally, the sheath defines a working channel adapted for passage of fluids between tissue distal to a distal end of the sheath and a proximal end of the sheath.

There is further provided in accordance with an exemplary embodiment of the invention, a protective sheath adapted to cover an elongate medical probe, comprising an elongate sheath adapted to receive an insertion tube of a medical probe and isolate the insertion tube from body tissue and at least one imaging device mounted on the sheath.

Optionally, the at least one imaging device is mounted on a distal face of the sheath.

There is further provided in accordance with an exemplary embodiment of the invention, an endoscope assembly, comprising an endoscope having a power source and a power consuming element, which are not connected within the endoscope and a protective sheath covering the endoscope, including a conductive element which closes a circuit connecting the power source and the power consuming element.

BRIEF DESCRIPTION OF THE DRAWINGS

Exemplary non-limiting embodiments of the invention will be described with reference to the following description of the embodiments, in conjunction with the figures. Identical structures, elements or parts which appear in more than one figure are preferably labeled with a same or similar number in all the figures in which they appear, and in which.

DETAILED DESCRIPTION OF EXEMPLARY EMBODIMENTS

Figure 1:
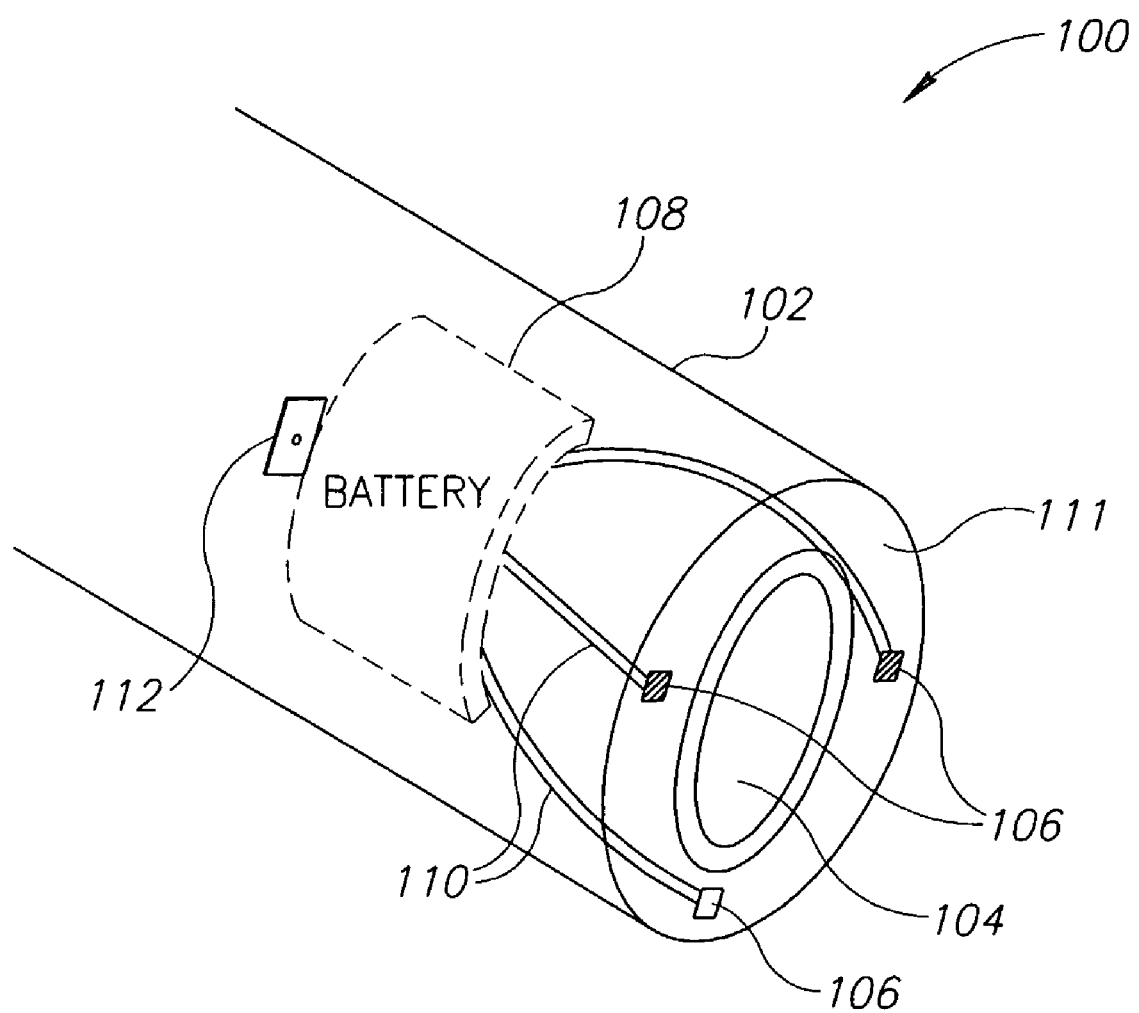
FIG. 1 is a schematic view of an endoscope sheath, in accordance with an exemplary embodiment of the invention.

FIG. 1 is a schematic view of an elongate endoscope sheath 100, in accordance with an exemplary embodiment of the invention. Endoscope sheath 100 includes a wall 102, which defines an internal lumen for receiving an insertion tube, and a distal window 104, which allows an imaging apparatus of an endoscope (or other elongate medical prove) within the sheath to view tissue outside the sheath. The imaging apparatus of the endoscope may be of any type known in the art, including a fiber optic bundle and/or a camera within the endoscope. One or more LEDs 106 are mounted on a distal face 111 of sheath 100, in order to provide illumination in a region viewed by an insertion tube within the lumen. In some embodiments of the invention, a battery 108 is embedded within wall 102, in order to provide power to LEDs 106, for example through wires 110.

In some embodiments of the invention, sheath 100 isolates an insertion tube inserted into the lumen, such that the insertion tube does not need to be cleaned and/or sterilized between patients.

Switch

Optionally, a switch 112 is used to connect battery 108 to LEDs 106 before or during a medical procedure, which uses sheath 100. In some embodiments of the invention, switch 112 automatically connects battery 108 to LEDs 106 when an insertion tube is inserted into sheath 100. Optionally, switch 112 includes a member protruding from the inner surface of wall 102 into the lumen that receives the insertion tube. When an insertion tube is inserted into the lumen, the insertion tube presses against the protruding member and connects battery 108 to LEDs 106. In some embodiments of the invention, the electrical circuit lighting LEDs 106 is missing a portion which is completed by a conductive plate on the endoscope. When the endoscope is inserted into the sheath in a proper orientation, the conductive plate closes the circuit and lights the LEDs.

Alternatively or additionally, switch 112 includes a protruding member on an outer surface of wall 102. When sheath 100 is inserted into a body cavity, the pressure of body tissue on the protruding member causes switch 112 to automatically connect battery 108 to LEDs 106.

Further alternatively or additionally, switch 112 is activated when sheath 100 is taken out of a sterile package, for example due to its being unfolded. In some embodiments of the invention, switch 112 includes a photoelectric cell and optionally an amplifying transistor which connects battery 108 to LEDs 106, when a sufficient amount of light impinges on the cell. The sterile package of sheath 100 is optionally opaque in this embodiment, so that opening the package activates battery 108. In these embodiments, once switch 112 connects battery 108 to LEDs 106, the LEDs continue to be lighted even after the actuation of the switch stops. For example, a capacitor or coil may be charged with sufficient power to keep the switch actuated for an entire procedure, for example at least 15 minutes, 30 minutes or even at least an hour. In another exemplary embodiment of the invention, the actuation moves the switch from an unconnected state into a stable connected state, for example mechanically.

In other embodiments of the invention, for example when switch 112 is activated by the insertion tube within the sheath and/or the sheath in the patient, battery 108 powers LEDs 106 only while switch 112 is activated, e.g., an insertion tube is within the lumen defined by wall 102.

In some embodiments of the invention, switch 112 is a human operated switch. Alternatively to switch 112 being located close to LEDs 106 at the distal end of sheath 100, the human operated switch is optionally located on a proximal end of sheath 100, which is not intended to be inserted into a patient and hence there is no problem of it being touched by a physician. Optionally, wires running along wall 102 connect the proximally located switch to battery 108 and LEDs 106. The wires running along wall 102 are optionally embedded within wall 102. Alternatively, the wires run within the lumen defined by sheath 100 between wall 102 and an endoscope within the sheath. Further alternatively or additionally, the wires run external to sheath 100, along the external surface of wall 102. In other embodiments of the invention, switch 112 allows wireless activation of LEDs 106, for example using a magnetic coupling circuit and/or any other wireless power receiver.

Optionally, switch 112 includes apparatus for only one of the above described activation methods. Alternatively, switch 112 includes apparatus that allows a plurality of different activation methods, which all need to be activated in order to light LEDs 106. Alternatively, any of the switches can be used to light LEDs 106. In some embodiments of the invention, different switches are used for different sub-groups of LEDs 106.

Wall and Embedded Battery

In some embodiments of the invention, wall 102 has a thickness of between about 0.2 to 0.6 millimeters. Battery 108 optionally has a thickness smaller than the thickness of wall 102, such that battery 108 may be embedded entirely within wall 102. Battery 108 optionally comprises a very thin battery as is known, for example, in the art of smartcards. In some embodiments of the invention, a lithium battery of a thickness less than 300 microns, such as described in PCT publication WO03/069700 or in US patent publication 2004/258984, the disclosures of which documents are incorporated herein by reference, is used.

Sheath 100 has a length according to the length of the medical probe inserted into the sheath. In an exemplary embodiment of the invention, sheath 100 is longer than 30 centimeters, 50 centimeters or even longer than 80 centimeters.

In other embodiments of the invention, wall 102 is thinner than 0.2 millimeters or even thinner than 0.1 millimeters. Optionally, a battery of a thickness of between about 0.04 millimeters and 0.08 millimeters is used. In these embodiments, a very thin battery which can be embedded within wall 102, is optionally used. Alternatively, wall 102 together with the battery embedded therein is thicker at a small portion in which the battery is embedded. Optionally, wall 102 itself is made thinner than other areas, in the area in which the battery is embedded.

Battery 108 optionally has an area and/or volume determined according to the required power of the battery for lighting LEDs 106. In some embodiments of the invention, battery 108 has an area of at least 0.5 square centimeters, 2 square centimeters, or even 5 square centimeters. Optionally, battery 108 has an area of less than 50 square centimeters or even less than 20 square centimeters. Battery 108 is optionally embedded in a relatively limited sector of wall 102, for example of less than 60° or even less than 30°, in order to minimize the loss of bendability of sheath 100 when battery 108 is stiffer than the sheath and/or to maintain a relatively small diameter of sheath 100. Alternatively, battery 108 covers over 180°, or even over 270° of the circumference of wall 102, so that battery 108 can have a larger area and hence a higher power level.

Alternatively to battery 108 being entirely embedded within wall 102 so that it does not protrude out of either side of the wall, battery 108 is only partially embedded and it protrudes out of sheath 100, for example on the outer side of the sheath. Alternatively, battery 108 protrudes out of the inner wall of sheath 100.

Figure 4:
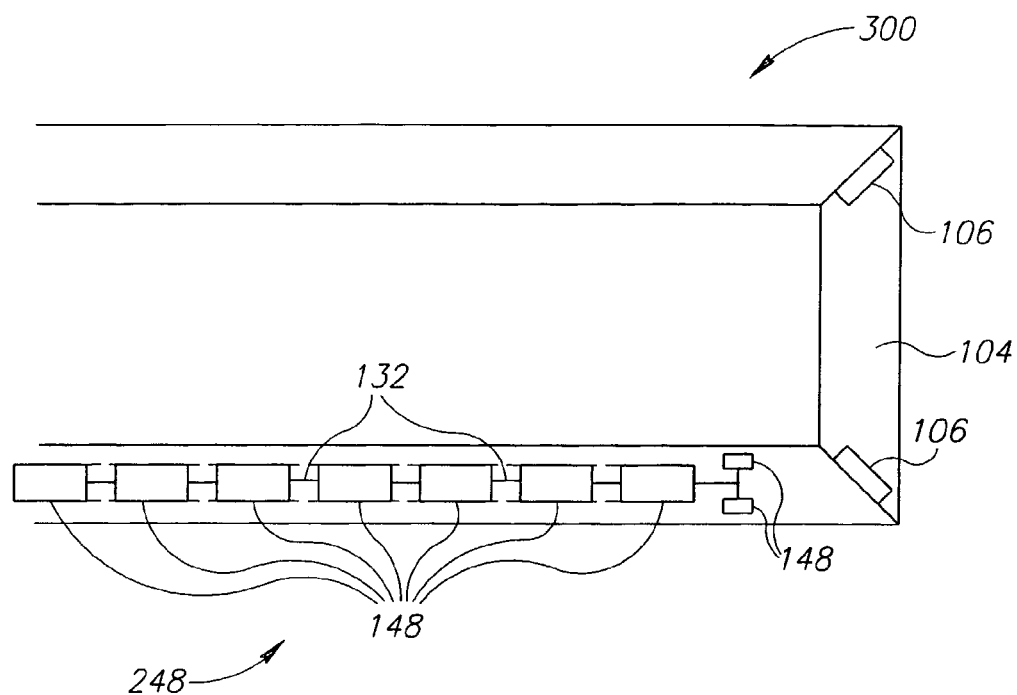
FIG. 4 is a sectional view of a sheath, in accordance with another exemplary embodiment of the invention.
Figure 5:
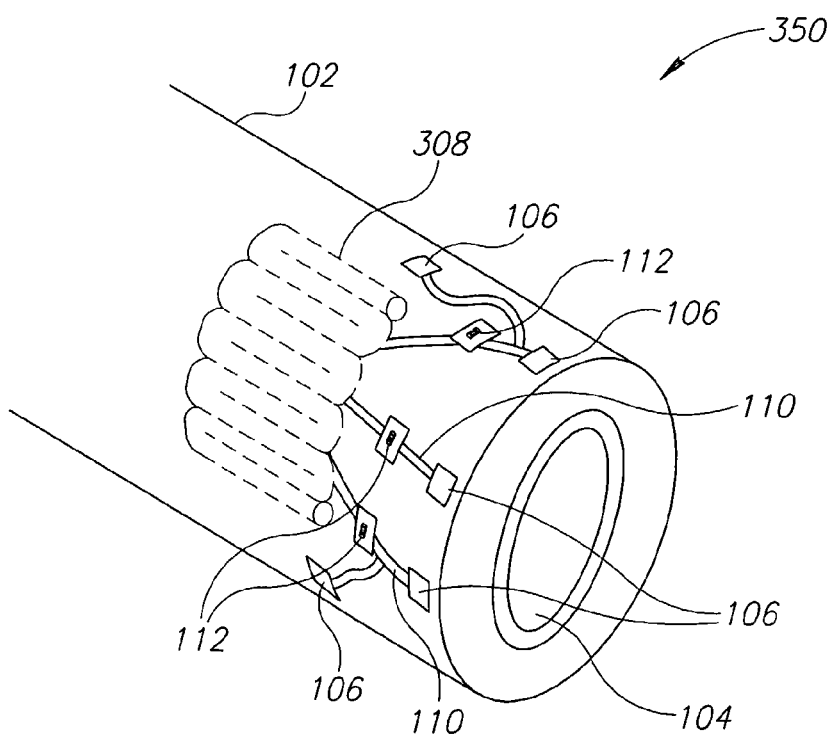
FIG. 5 is a schematic illustration of a protective sheath, in accordance with another exemplary embodiment of the invention.

Battery 108 is optionally at least as flexible as sheath 100. Alternatively, battery 108 is less flexible than sheath 100. Optionally, in accordance with this alternative, battery 108 is laid out within sheath 100, in a manner which minimizes the limitation of flexibility of sheath 100 due to the embedding of battery 108. In an exemplary embodiment of the invention, the battery covers only a small portion of the circumference of sheath 100. Optionally, the battery is long relative to its width, for example having a length at least 10 times or even 20 times as long as its width. Alternatively or additionally, the battery is long and narrow, folded in a back and forth manner (i.e., in the form of a series of alternately oriented "U"s), as shown in FIG. 5. Alternatively or additionally, the battery is segmented axially and/or circumferentially, as shown in FIG. 4. In some embodiments of the invention, the battery is formed of intermittent wide and narrow sections and/or intermittent thin and thick sections, in order to increase the flexibility of the battery.

Alternatively to a single wall 102, sheath 100 is replaced by a sheath assembly including two walls, between which battery 108 is embedded. Alternatively to a sheath assembly including two walls over its entire area, two walls are used only in localities where things are embedded, for example where battery 108 is embedded.

Alternatively or additionally to embedding battery 108 in wall 102, at least part of a battery is mounted on, or embedded in, distal face 111 of the sheath. In accordance with this embodiment, distal face 111 is optionally relatively thick in order to accommodate the battery.

LEDs

The number of LEDs 106 mounted on sheath 100 and/or the arrangement of the LEDs is optionally directed at maximizing the light on a body portion viewed by an insertion tube within sheath 100, through window 104. For example, any of the LED arrangements in the above mentioned U.S. patents, may be used. In some embodiments of the invention, all the LEDs provide light at the same wavelengths. Alternatively, different LEDs provide light at different wavelengths. In an exemplary embodiment of the invention, LEDs 106 have a surface area of less than 0.5 square millimeters, optionally even less than 0.1 square millimeters.

Wireless Power Port

Figure 2:
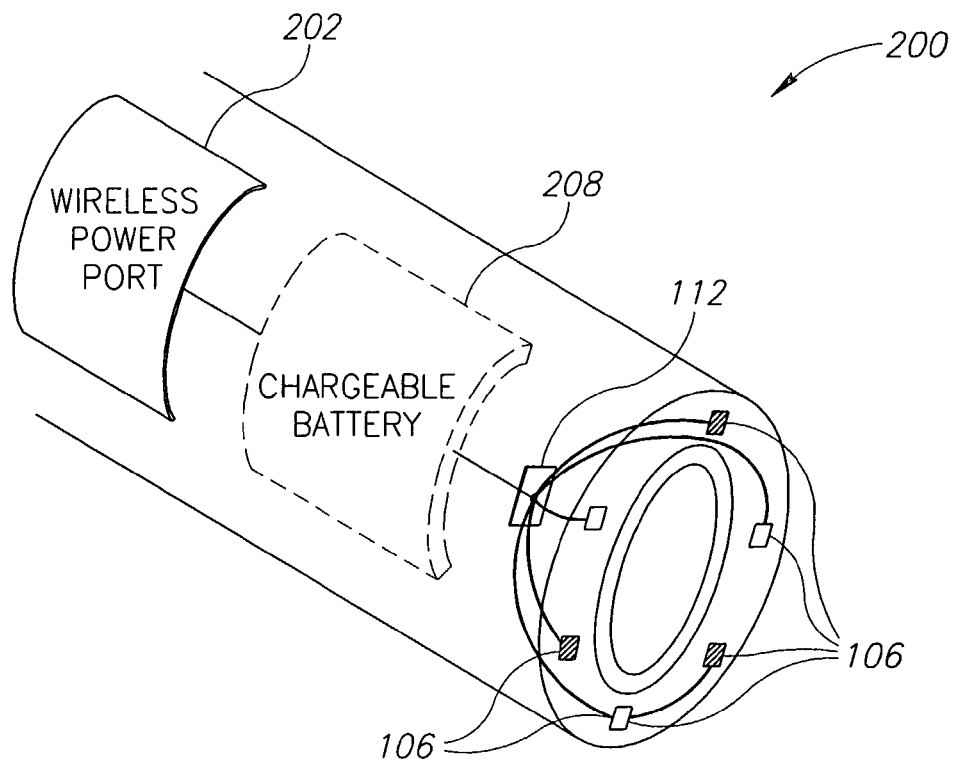
FIG. 2 is a schematic illustration of a protective sheath, in accordance with another exemplary embodiment of the invention.

FIG. 2 is a schematic illustration of a protective sheath 200, in accordance with another exemplary embodiment of the invention. Protective sheath 200 is similar to sheath 100, but includes a wireless power reception port 202 which is used to wirelessly receive power from an external power source.

In some embodiments of the invention, sheath 200 is supplied with a chargeable battery 208 which is optionally precharged for use. Alternatively or additionally, a capacitor is used. If, during an endoscopic procedure, LEDs 106 do not provide illumination (or sufficient illumination), battery 208 is charged through power reception port 202. The charging is optionally performed under instructions of a physician controlling the endoscope. Alternatively, an automatic charger periodically or continuously transfers power to battery 208 according to an expected power dissipation rate. Further alternatively, feedback is transmitted from the LEDs and/or battery on the level of the illumination, and accordingly automatic charging of battery 208 is carried out.

Alternatively to a precharged battery, sheath 202 is supplied with a battery which is not charged. In preparation for an invasive procedure and/or during the insertion of the sheath into the patient, battery 208 is charged. In some embodiments of the invention, in accordance with this alternative, switch 112 is not included in sheath 200. Further alternatively, sheath 200 does not include a battery and LEDs 106 are directly powered by power received through port 202.

In some embodiments of the invention, power reception port 202 includes a coil for receiving electrical energy through electromagnetic coupling. Alternatively or additionally, port 202 includes a flat surface electrode, which is sufficiently large to allow inducing currents therein, for example via electromagnetic coupling. The induced currents optionally charge battery 208 and/or light up LEDs 106. Further alternatively or additionally, port 202 operates on any other wireless power transfer method, such as any of the methods known in the field of smart cards and/or any of the methods discussed in above mentioned U.S. provisional patent application 60/632,739, filed Dec. 1, 2004.

It is noted that FIG. 2 illustrates variations relative to FIG. 1 other than the addition of power reception port 202. FIG. 2 illustrates six LEDs 106, in order to illustrate that sheath 100 or 200 may carry substantially any number of desired LEDs 106, including more than five, more than 10, or even more than 20 LEDs. In other embodiments of the invention, sheath 200 carries only a single LED 106. FIG. 2 further shows switch 112 between battery 208, rather than proximal to battery 208. This illustrates the fact that switch 112 may be located substantially anywhere in sheath 100 or 200 where it is convenient to control the connection between battery 108 or 208 and LEDs 106.

Alternatively or additionally to switch 112 connecting battery 108 to LEDs 106, switch 112 activates the battery, for example as is known in the art of life vests and/or rockets. In an exemplary embodiment of the invention, switch 112 opens a valve of an electrolyte sack, which fills the battery, for use. Optionally, in this embodiment, the battery is operated upon opening of the sterile package of the sheath, automatically and/or by an act of a physician using the sheath.

Alternatively or additionally to a wireless power reception port 202, wires passing from a proximal end of sheath 200 are used to charge battery 208.

Figure 3:
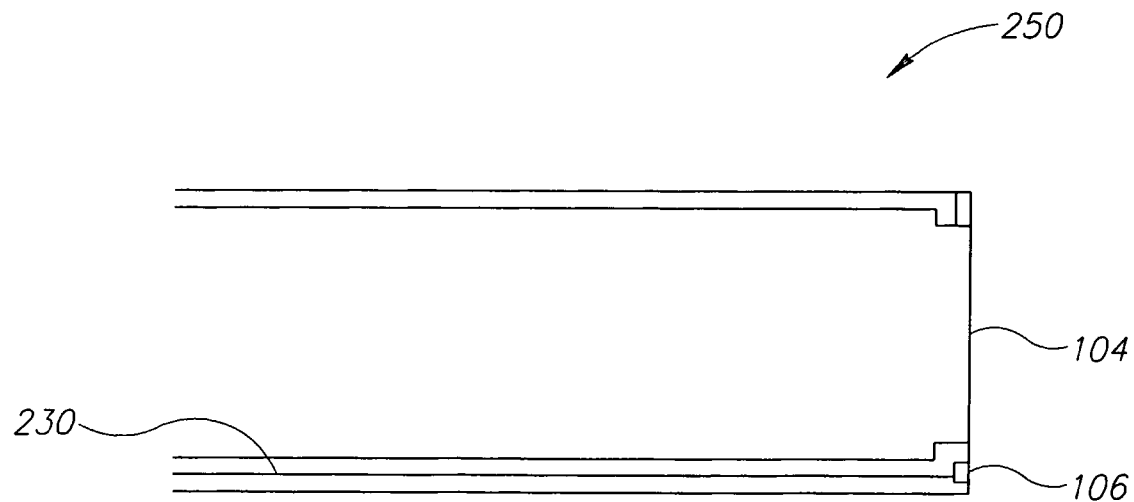
FIG. 3 is a sectional view of a sheath, in accordance with another exemplary embodiment of the invention.

FIG. 3 is a sectional view of a sheath 250, in accordance with another exemplary embodiment of the invention. Sheath 250 does not include a battery, but rather uses wires 230 running from a proximal end of sheath 250, to a distal end of the sheath to lead electrical power from an external power source to a LED 106.

In some embodiments of the invention, the LEDs of a sheath are connected to an electrical socket in the sheath, which is adapted to mate with a plug in an endoscope, covered by the sheath. Alternatively or additionally to a socket, any other mating electrical contacts may be used, for example with prongs or bare contacts. Optionally, wires run along the endoscope and connect the plug to an external power source. Alternatively, a power source is carried within the endoscope. Alternatively to a socket on the sheath and a plug on the endoscope, any other mating apparatus may be used to form electrical contact between power provided through the endoscope and LEDs on the sheath. In some embodiments of the invention, power for the LEDs is received from both a battery in the endoscope and a battery in the sheath.

FIG. 4 is a sectional view of a sheath 300, in accordance with another exemplary embodiment of the invention. In sheath 300, LEDs 106 are embedded within window 104. Optionally, LEDs 106 are oriented diagonally in order to direct their light toward a body portion viewed by an insertion tube within sheath 300.

In some embodiments of the invention, sheath 300 includes optic elements (e.g., lenses, reflective surfaces) which direct the light from LEDs 106 in a desired direction.

Sheath 300 further illustrates a battery pack 248, which is segmented in order to increase the flexibility of sheath 300. In some embodiments of the invention, battery pack 248 comprises a plurality of battery links 148, connected through wire segments 132. Optionally, the battery links 148 are arranged axially along the sheath. Alternatively or additionally, a plurality of battery links 148 are arranged adjacent each other concentrically at a same position along the length of the sheath.

FIG. 5 is a schematic illustration of a protective sheath 350, in accordance with another exemplary embodiment of the invention. Sheath 350 includes a plurality of LEDs 106 displaced on wall 102 adjacent the distal end of sheath 350. Optionally, at least some of LEDs 106 are located within 10 centimeters or even 5 centimeters from the distal end of sheath 350. In some embodiments of the invention, LEDs 106 are located within 1-2 centimeters from the distal end of the sheath. LEDs 106 on wall 102 are optionally used in organs in which the illumination from the LEDs 106 reaches tissue to be viewed, for example, when a viewing apparatus within the sheath is oriented sideways to view through wall 102, rather than through window 104.

Sheath 350 includes a battery 308 that is long and narrow, folded in a back and forth manner (i.e., in the form of a series of alternately oriented "U"s). The battery is optionally close to LEDs 106, so that there is no need for long wires running along the length of sheath 350. Optionally, battery 108 is distanced from LEDs 106 by less than 10 centimeters, 5 centimeters or even 3 centimeters. In some embodiments of the invention, battery 104 is distanced from the distal end of sheath 350 by less than 4 centimeters or even less than 2 centimeters. Alternatively, to allow for more space for the battery, the battery is embedded toward the proximal end of the sheath, for example on the proximal half of the portion of the sheath inserted into the patient.

In the above description, for simplicity, the sheaths were shown without internal working channels. It will be understood by those skilled in the art that any of the sheaths described above may be modified to include one or more working channels and/or any other apparatus which is suitable for incorporation in a protective sheath.

Figure 6:
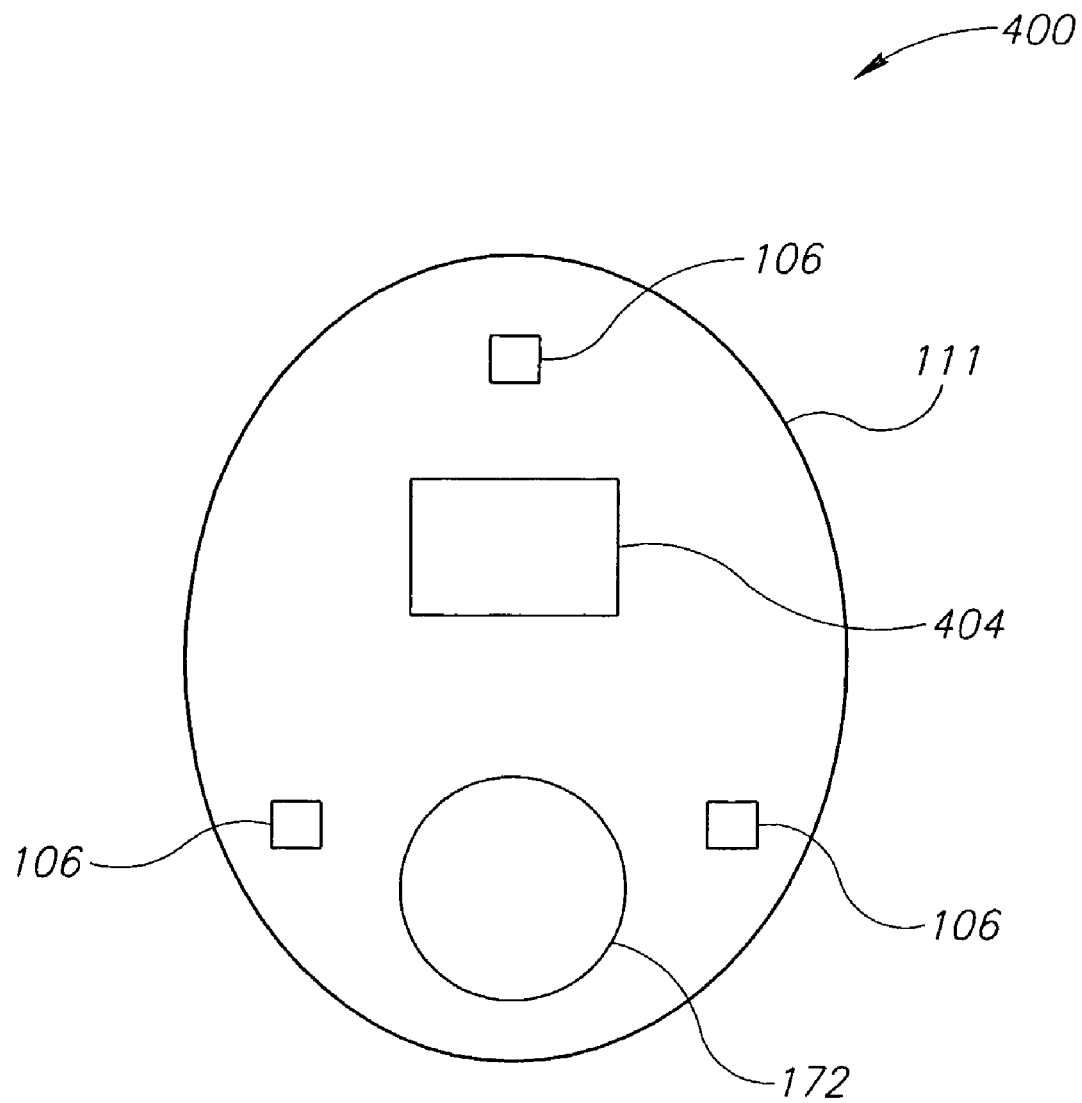
FIG. 6 is a top view of a sheath, in accordance with another an exemplary embodiment of the invention.

FIG. 6 is a top view of a sheath 400, in accordance with an exemplary embodiment of the invention. Sheath 400 carries LEDs 106 on its distal face 111 along with a thin camera (e.g., CMOS, CCD) 404. Camera 404 is optionally powered by a battery embedded in sheath 400 and/or receives power using any of the other methods described herein. In some embodiments of the invention, camera 404 transmits the images it acquires wirelessly. Alternatively, the acquired images are transferred through wires running along the sheath to a proximal end of the sheath. A channel 172 allows insertion of tools and/or fluids through the sheath to its distal end. The channel may also be used for suction and/or other tasks.

Although in the above description the battery and/or power port is used to power LEDs, the power port and/or battery may be used to power other light generation sources, such as electro-luminescent and/or plasma sources.

In some embodiments of the invention, a sheath includes a miniature chemiluminescent vial that provides illumination. The vial is optionally activated by shaking the sheath after the sheath is removed from its sterilized package. Alternatively, the vial may be activated using any other method known in the art. The chemiluminescent vial is optionally produced using any of the chemicals and/or structures described in any of U.S. Pat. No. 5,819,727 to Linder, U.S. Pat. No. 6,496,718 to Lonky, RE35,132 to Bay et al., U.S. Pat. No. 5,179,938 to Lonky, U.S. Pat. No. 6,247,995 to Bryan and U.S. Pat. No. 3,597,363 to Avella, the disclosures of all of which are incorporated herein by reference. In an exemplary embodiment of the invention, the sheath defines an annular chemiluminescent between inner and outer walls of the sheath, along a distal axial portion of the sheath. Alternatively or additionally, a chemiluminescent vial is included in at least a portion of the distal face of the sheath.

Further alternatively, the battery and/or power port are used to power other elements embedded in the sheath, such as ablation electrodes, a control circuit, cameras, sensors (e.g., temperature sensors, power sensors) and/or electrical signal sensing apparatus and/or wireless circuits for transmission of sensed signals to an external data collection unit.

Alternatively to using a battery, a sheath may include any other power source, such as a piezo-electric power source which converts pressure on the sheath and/or movements of the sheath into electrical power.

In some embodiments of the invention, a sheath is used to provide an electrical contact between electrical ports of an endoscope. For example, an electrical contact between a power source of the endoscope and LEDs of the endoscope may require a conductive patch on a sheath. Thus, the endoscope does not operate, unless a matching sheath covers the endoscope and provides protection from contamination. This serves as a safety measure preventing use of the invasive probe without a sheath. In some embodiments of the invention, the electrical contacts on the sheath span over the entire circumference, so that the operation of the endoscope is not dependent on the orientation of the sheath. Alternatively, the sheath needs to be loaded on the probe in a specific orientation.

The protective sheath is optionally formed of a durable material which does not tear under normal pressures on invasive probes within patients. Alternatively or additionally, the protective sheath is not permeable to germs and other contaminations. In some embodiments of the invention, the protective sheath is longer than the length of the portion of the invasive tube adapted for insertion into the patient or at least of the portion of the invasive tube actually inserted into the patient.

Although the above description relates to protective sheaths which isolate invasive tubes from contaminated tissue, in some embodiments of the invention, other sheaths are used. For example, a sheath primarily employed for mounting a battery or LED on an invasive probe, may be used. In some embodiments of the invention, a sheath having a tube shape without a distal end used. Optionally, the non-protective sheath covers at least 50%, 70% or even 90% of the portion of the invasive probe inserted into the patient. In some embodiments of the invention, the sheath (protective or non-protective) has a length of at least 50 centimeters, 75 centimeters or even a meter.

It will be appreciated that the above-described methods may be varied in many ways. For example, the sheaths of the present invention may be used with elongate medical invasive probes other than endoscopes, such as catheters. It should also be appreciated that the above described description of methods and apparatus are to be interpreted as including apparatus for carrying out the methods, and methods of using the apparatus.

The present invention has been described using non-limiting detailed descriptions of embodiments thereof that are provided by way of example and are not intended to limit the scope of the invention. It should be understood that features and/or steps described with respect to one embodiment may be used with other embodiments and that not all embodiments of the invention have all of the features and/or steps shown in a particular figure or described with respect to one of the embodiments. Variations of embodiments described will occur to persons of the art. Furthermore, the terms "comprise," "include," "have" and their conjugates, shall mean, when used in the claims, "including but not necessarily limited to."

It is noted that some of the above described embodiments may describe the best mode contemplated by the inventors and therefore may include structure, acts or details of structures and acts that may not be essential to the invention and which are described as examples. Structure and acts described herein are replaceable by equivalents which perform the same function, even if the structure or acts are different, as known in the art. Therefore, the scope of the invention is limited only by the elements and limitations as used in the claims.

The invention claimed is:

1. A protective sheath adapted to cover an elongate medical probe, comprising:
    an elongate sheath adapted to receive an insertion tube of a medical probe; and
    at least one light generating element mounted on the sheath,
    wherein the at least one light generating element is mounted within three centimeters of a distal end of the sheath.

2. A sheath according to claim 1, wherein the at least one light generating element comprises at least one light emitting diode.

3. A protective sheath adapted to cover an elongate medical probe, comprising:
    an elongate sheath adapted to receive an insertion tube of a medical probe; and
    at least one light generating element mounted on the sheath,
    wherein the at least one light generating element comprises at least one chemiluminescent vial.

4. A protective sheath adapted to cover an elongate medical probe, comprising:
    an elongate sheath adapted to receive an insertion tube of a medical probe;
    at least one light generating element mounted on the sheath; and
    a battery electrically coupled to the light generating element, at least partially embedded within the sheath.

5. A sheath according to claim 1, wherein the at least one light generating element is mounted on a distal face of the sheath.

6. A sheath according to claim 1, comprising a battery electrically coupled to the light generating element, at least partially embedded within the sheath.

7. A sheath according to claim 1, comprising at least one optic element adapted to change a direction of light emitted by one or more of the at least one light generating element.

8. A sheath according to claim 1, wherein the elongate sheath comprises a protective sheath suitable to isolate the insertion tube from body tissue.

9. A protective sheath according to claim 1, adapted to, comprising:
at least one imaging device mounted on the sheath,
wherein the elongate sheath is adapted to isolate the insertion tube from body tissue.

10. A sheath according to claim 9, wherein the at least one imaging device is mounted on a distal face of the sheath.

11. A protective sheath for an endoscope, comprising:
an elongate sheath adapted to receive an insertion tube of an endoscope and isolate the insertion tube from body tissue; and
a power source at least partially embedded within the sheath.

12. A sheath according to claim 11, wherein the power source comprises a battery.

13. A sheath according to claim 12, wherein the battery is at least partially embedded within the sheath within five centimeters from a distal end of the sheath.

14. A sheath according to claim 12, wherein the battery is rechargeable.

15. A sheath according to claim 12, wherein the battery has a length at least ten times longer than its width.

16. A sheath according to claim 12, wherein the battery comprises a plurality of links connected through wires.

17. A sheath according to claim 12, wherein the battery does not substantially affect the flexibility of the sheath.

18. A sheath according to claim 11, comprising a wireless power reception port, coupled to the sheath, adapted to wirelessly receive power from a power transmitter external to the sheath.

19. A sheath according to claim 11, wherein the sheath defines a working channel adapted for passage of fluids between tissue distal to a distal end of the sheath and a proximal end of the sheath.

20. An endoscope assembly, comprising:
an endoscope having a power source and a power consuming element, which are not connected within the endoscope; and
a protective sheath covering the endoscope, including a conductive element which closes a circuit connecting the power source and the power consuming element,
wherein the protective sheath connects the power source to the power consuming element regardless of the relative radial orientation of the sheath and the endoscope.

21. An assembly according to claim 20, wherein the power consuming element comprises an illumination unit.

22. A sheath according to claim 4, wherein the at least one light generating element is mounted within three centimeters of a distal end of the sheath.

23. A sheath according to claim 4, comprising at least one optic element adapted to change a direction of light emitted by one or more of the at least one light generating element.

24. A sheath according to claim 4, wherein the elongate sheath comprises a protective sheath suitable to isolate the insertion tube from body tissue.

* * * * *